(12) United States Patent
Goel

(10) Patent No.: US 10,646,477 B1
(45) Date of Patent: May 12, 2020

(54) 5-SUBSTITUTED 2,4-THIAZOLIDINEDIONES (THIOHYDANTOINS), PSEUDOTHIOHYDANTOINS, AND PROPSEUDOTHIOHYDANTOINS FOR USE AS ANTIVIRAL AGENTS

(71) Applicant: Jiva Pharma, Inc., Ann Arbor, MI (US)

(72) Inventor: Om P Goel, Ann Arbor, MI (US)

(73) Assignee: Jiva Pharma, Inc., Ann Arbor, MI (US)

( * ) Notice: Subject to any disclaimer, the term of this patent is extended or adjusted under 35 U.S.C. 154(b) by 0 days.

(21) Appl. No.: 15/990,049

(22) Filed: May 25, 2018

Related U.S. Application Data

(63) Continuation-in-part of application No. 15/283,422, filed on Oct. 2, 2016, now abandoned.

(60) Provisional application No. 62/243,045, filed on Oct. 17, 2015.

(51) Int. Cl.
| | |
|---|---|
| *A61K 31/195* | (2006.01) |
| *A61K 31/426* | (2006.01) |
| *C07C 335/32* | (2006.01) |
| *A61K 9/08* | (2006.01) |
| *A61K 9/48* | (2006.01) |
| *A61P 31/22* | (2006.01) |
| *A61K 9/06* | (2006.01) |
| *A61K 31/522* | (2006.01) |

(52) U.S. Cl.
CPC .............. *A61K 31/426* (2013.01); *A61K 9/06* (2013.01); *A61K 9/08* (2013.01); *A61K 9/4825* (2013.01); *A61P 31/22* (2018.01); *C07C 335/32* (2013.01); *A61K 31/522* (2013.01); *A61K 2300/00* (2013.01)

(58) Field of Classification Search
CPC .................................................... A61K 31/195
USPC ......................................................... 514/562
See application file for complete search history.

(56) References Cited

U.S. PATENT DOCUMENTS 9,364,465 B2  6/2016  Goel

FOREIGN PATENT DOCUMENTS

| | | |
|---|---|---|
| WO | 2014/160936 | 10/2014 |
| WO | 2015/042495 | 3/2015 |

OTHER PUBLICATIONS

PubChem CID 81890 (Year: 2005).*

(Continued)

*Primary Examiner* — Shengjun Wang
(74) *Attorney, Agent, or Firm* — Technology Law, PLLC; Karen L Kimble

(57) ABSTRACT

The present invention concerns the synthesis and use of formulations of 5-substituted 2, 4-thiazolidinediones, pseudothiohydantoins, and propseudothiohydantoins and 2, 4-thiazolidinediones metforminate salts for topical and systemic treatments of infections caused by herpes simplex viruses and varicella zoster viruses.

8 Claims, 10 Drawing Sheets
(10 of 10 Drawing Sheet(s) Filed in Color)

(56) References Cited

OTHER PUBLICATIONS

T. Tomsic and L.P. Masic, "Rhodanine as a Privileged Scaffold in Drug Discovery", Current Medicinal Chemistry, 2009, 16, 1596-1629.

O. V. Bakbardina et al., "Synthesis and Fungicidal Activity of Pseudo-Thiohydantoins, Their 5-Arylidene Derivatives, and 5-Arylidene-3-b-Aminothiazolid-2,4-One Hydrochlorides", Pharmaceutical Chemistry Journal, 2006, 40 (10), 357-359.

Mark N. Prichard et al., "A microtiter virus yield reduction assay for the evaluation of antiviral compounds against human cytomegalovirus and herpes simplex virus", Journal of Vitological Methods, 1990, 28, 101-106.

* cited by examiner

|  | JNA 0042 15mM | Percent Reduction | JNA 0042 7.5mM | Percent Reduction |
|---|---|---|---|---|
|  | 1.50E+03 | 99.9998718 | 2.50E+04 | 99.9978632 |
|  | 2.50E+03 | 99.9997863 | 3.00E+04 | 99.9974359 |
|  | 3.00E+03 | 99.9997436 | 2.00E+04 | 99.9982906 |
| Average % Reduction | 2.33E+03 | 99.9998006 | 2.50E+04 | 99.9978632 |
| STD DEVIATION | 7.64E+02 | 0.00006528 | 5.00E+03 | 0.000427350 |

|  | JNA 0005 20mM | Percent Reduction | JNA 0005 10mM | Percent Reduction |
|---|---|---|---|---|
|  | 2.55E+03 | 99.9997821 | 2.50E+05 | 99.9786325 |
|  | 2.20E+03 | 99.9998120 | 2.46E+05 | 99.9799598 |
|  | 1.90E+03 | 99.9998376 | 2.60E+05 | 99.9777778 |
| Average % Reduction | 2.22E+03 | 99.9998105 | 2.52E+05 | 99.9784900 |
| STD DEVIATION | 3.25E+02 | 0.00002781 | 7.64E+03 | 0.000652789 |

Figure 7

5-SUBSTITUTED 2,4-THIAZOLIDINEDIONES (THIOHYDANTOINS), PSEUDOTHIOHYDANTOINS, AND PROPSEUDOTHIOHYDANTOINS FOR USE AS ANTIVIRAL AGENTS

FIELD OF THE INVENTION

The present invention concerns the formulations of 5-substituted-2,4-thiazolidinediones (thiohydantoins), pseudothiohydantoins, propseudothiohydantoins and their metforminate salts, for topical and systemic treatments of infections caused by viruses such as herpes simplex viruses (HSV1, HSV2), varicella zoster virus (VZV), ebola and adeno viruses and other viruses.

BACKGROUND OF THE INVENTION

Herpes simplex is a viral disease from the herpesviridae family caused by both Herpes simplex virus type 1 (HSV-1) and type 2 (HSV-2). Infection with the herpes virus is categorized into one of several distinct disorders based on the site of infection. Oral herpes, herpes labialis, the visible symptoms of which are commonly called cold sores or fever blisters, is an infection of the face or mouth. Herpes labialis, usually caused by HSV-1, occurs in approximately 90% of cases and affects 20-45% of the adult US population. There is one US Food and Drug Administration (US FDA) approved topical product, docosanol, which is currently available as a therapeutic treatment. Systemically administered acyclovir, penciclovir, valacyclovir or famciclovir are also approved for use in speeding the healing of herpes labialis. Since recurrences occur over the lifetime of infected patients, developing additional topical and systemic antiviral therapies is needed.

Genital herpes, known as herpes genitalis or simply as herpes (from HSV-2), is the second most common and painful form of herpes, although either of these virus may cause both infections. Other disorders, such as herpetic whitlow, herpes gladiatorum, ocular herpes, cerebral herpes infection encephalitis, Mollaret's meningitis, neonatal herpes, and possibly Bell's palsy, are all caused by herpes simplex viruses. Herpes simplex is most easily transmitted by direct contact with a lesion or the body fluid of an infected individual. In 2013 about 1.1 billion people (15.9%) had asymptomatic genital herpes and 47 million new cases of genital herpes occurred (WIKI).

Varicella zoster virus or varicella-zoster virus (VZV) is one of eight herpes viruses known to infect humans and vertebrates. VZV only affects humans and commonly causes chickenpox in children, teens and young adults whereas herpes zoster (shingles) occurs in adults and rarely in children. VZV is known by many names, including chickenpox virus, varicella virus, zoster virus, and human herpes virus type 3 (HHV-3). Shingles is characterized by a painful skin rash with blisters in a large localized area on one side of the body, which may take 2-4 weeks to heal. Ongoing nerve pain following the shingles infection may last for months. The shingles vaccine, Zostavax® (a trademark of Merck Sharp & Dohme Corp.) decreases the incidence of shingles by about half in those between the ages of 50 and 80. (WIKI) In 2017, the US FDA approved SHINGRIX® (trademark of GlaxoSmithKline Biologicals, S.A.), a vaccine indicated for prevention of shingles (herpes zoster) in adults aged 50 years and older with >90% efficacy. It is available worldwide.

Present Treatments

There are presently no known methods to eradicate the herpes virus from the body. The herpes virus survives, dormant in nerve cells, and can be reactivated at any time, causing another outbreak at or near the initial infection site. With time, the frequency and severity of herpes outbreaks may diminish as antiviral immunity in the host grows. The duration of a cold sore from first appearance to healing is about 10 days, even without treatment. The herpes genitalis outbreak may cover larger areas, and take 2-3 weeks when existing ulcers crust and heal.

There are no treatments for the outbreak of shingles in a person once it appears. Use of over-the-counter (OTC) analgesics or opioids alleviates pain (WIKI)

Topical Treatments

1-Docosanol, a 22 carbon straight-chain saturated fatty alcohol, also known as behenyl alcohol, used traditionally as an emollient, emulsifier and thickener in cosmetics, is approved by the US FDA as Abreva® (trademark of GlaxoSmithKline Consumer Healthcare), an antiviral agent for reducing the duration of cold sores caused by the herpes simplex virus. Pharmacological formulations of 1-docosanol are complex, due to its near zero aqueous solubility, and its anti-HSV activity is difficult to reproduce in vitro, as described (Antiviral activity of 1-docosanol, an inhibitor of lipid-enveloped viruses including herpes simplex; Mohammed H. Khalil, et al.; Proc. Natl. Acad. Sci. USA Vol. 88, pp. 10825-10829, December 1991). Other publications have used surfactants such as Pluronic F-68 or Tetronic 908 and in these papers, the 50% inhibition ranges merely from 4 mM to 15 mM. Even in dimethyl sulfoxide as solvent, 1-docosanol makes only a milky suspension (even after sonication).

1-Docosanol is thought to act by inhibiting the fusion of the human host cell with the viral envelope of the herpes virus, thus preventing its replication (WIKI). The drug is available OTC as a cream. It is reported to reduce the mean time of healing to 4.1 days. The side-effects are mild headaches. The most serious side effects, although rare, are allergic reactions, including difficulty breathing, confusion, facial swelling, fainting, dizziness, hives or chest pain (WIKI).

Acyclovir or aciclovir is an acycloguanosine antiviral marketed under trade names such as Cyclovir, Herpex, Acivir, Acivirax, Zovirax® (trademark of GlaxoSmithKline LLC), Xovir and Imavir, are the most commonly used systemic antiviral drugs. Cream preparations, 5%, are used primarily for labial herpes simplex. These formulations are not very effective, however. Also, the topical creams are difficult to apply evenly over the infected surface, undesirably visible, and sensed or intrusive on the mind. Primarily, acyclovir and its prodrug, valacyclovir, are excellent oral therapies widely used in treating herpes genitalis infections.

Trifluridine, a 3-deoxynucleoside, is the mainstay of therapy to treat severe herpes infections of the eye. It is usually prescribed in the form of eye drops, and instilled at least 5 times daily for a few days. Due to the complex synthesis of trifluoridine, these prescriptions are very expensive.

Clearly, there's need for effective new treatments to treat skin and ocular infections caused by the HSV and VZV viruses. It is also desirable if these treatments were water and/or glycols soluble, to be applied as eye drops for treating herpes simplex keratitis and as clear gels or creams to apply over areas of infections as in oral herpes and herpes genitalis. Clear gels are less visible, easier to apply due to lower viscosity, and more acceptable than creams to treat infections of herpes labiliasis. The gels may also be developed in the form of patches of dissolvable microneedles for transdermal drug delivery. Particularly useful would be oral and/or parenteral treatments to treat incipient cases of infections caused by the varicella zoster virus (VZV).

BRIEF DESCRIPTION OF THE INVENTION

The present invention provides a method of treating herpes simplex virus and herpes varicella zoster infections comprising administering to a person in need of such treatment a therapeutically effective amount of a pharmaceutically-acceptable formulation having as the therapeutic agent compounds of Formula (I), 5-substituted thiohydantoins; or Formula (II), 5-substituted pseudothiohydantoins, which form as stable, synthetic precursors of compounds of Formula (I); or Formula (III) which, in a few cases, are isolated as novel, stable intermediates from synthesis of Formula (II) compounds, and are referred to in this present application as propseudothiohydantoins. The structures of these compounds are as follows:

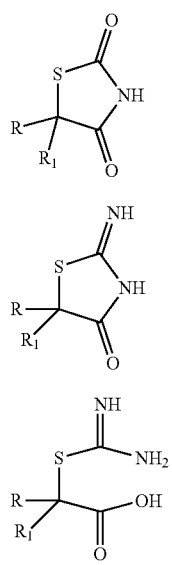

Formula (I)

Formula (II)

Formula (III)

wherein:
R and $R_1$ are each independently H; F; Cl; $CH_3$; $CF_3$; $C_1$-$C_6$ straight-chain or branched alkyls; $C_6$-$C_{10}$ aryl unsubstituted or substituted with $C_1$-$C_6$ straight chain or branched $C_1$-$C_6$ alkyls; $C_1$-$C_6$ alkoxyl; halo (fluoro, chloro); $C(O)CH_3$; or $NHC(O)CH_3$; and R and $R_1$ may be tethered together to form 3- to 7-membered alicyclic rings; and when R is H, and $R_1$ is a group as defined above other than H, then both R- and S-stereoisomers are included; and when R is H, then $R_1$ may be an omega-3 polyunsaturated fatty acid (PUFA) derivative, which is joined from the methylene moiety formed by reduction of the carboxylic acid of one of the following representative omega-3 polyunsaturated fatty acids:

cis,cis,cis-9,12,15-octadecatrienoic acid (ALA), providing RS-5-((9Z,12Z,15Z)-octadeca-6,9,12-trien-1-yl)thiazolidine-2,4-dione;

cis,cis,cis,cis-5,8,11,14,17-eicosapentanenoic acid (EPA), providing RS-5-((5Z,8Z,11Z,14Z,17Z)-eicosa-5,8,11,14,17-pentaen-1-yl)thiazolidine-2,4-dione; and cis,cis,cis,cis,cis,cis-4,7,10,13,16,19-docosahexaenoic acid (DHA), providing RS-5-((4Z,7Z, 10Z,13Z,16Z, 19Z)docosa-4,7,10,13,16,19-hexaen-1-yl)thiazolidine-2,4-dione; and including the metforminate salts of Formula (I) or Formula (II) or pharmaceutically-acceptable water soluble salts, such as sodium, potassium or calcium salts, of Formula (I), (II) or (III).

Compounds of Formula (II) are 2-iminothiohydantoins, known in the chemical literature as pseudothiohydantoins, and may be isolated as intermediates from the synthesis of compounds of Formula (I). These pseudothiohydantoins are often stable, but may be hydrolyzed to compounds of Formula (I) by heating in aqueous acids such as hydrochloric or sulfuric acid (see, for example, Ge No Meng et al., *Organic Preparations and Procedures International* 43(3): 312-313, January 2011). Surprisingly, it was discovered that the 2-iminothiohydantoin or pseudothiohydantoin, of Formula (II), where R and $R_1$ are both H, had the most in vitro antiviral activity against HSV-1 and HSV-2; $EC_{50}$ of 296 µM and 76 µM, and safety index, $SI_{50}$ of 66 µM, and 255 µM, respectively.

Compounds of Formula (III), designated in this present application as propseudothiohydantoins, may be isolated in some cases as stable intermediates from the synthesis of compounds of Formula (II). For example, when R is H, and $R_1$ is F, the compound RS-(Carbamimidoylsulfanyl)(fluoro) acetic acid or 2-[Amino(imino)methylsulfenyl]-2-fluoroacetic acid (JIVA-0043), was isolated, which is an example of a propseudothiohydantoin of Formula (III). Similarly, RS-2-[Amino(imino)methylsulfenyl]-2-phenylacetic acid (JIVA-0045), is an example of a propseudothiohydantoin of Formula (III). However, it was not possible to cyclize JIVA-0043 to the corresponding pseudothiohydantoin compound of Formula (II) under numerous dehydrating reaction conditions, including use of versatile carbodiimide type of reagents. These Formula (III) compounds are new and previously unknown for this present use as antiviral agents.

For some compounds of the present invention the various formulae can be understood as interrelated by their process for making the compound. Thus for preparing a compound of Formula (III), propseudothiohydantoins, as defined above, it can be prepared by reacting a thiourea and an alpha-substituted acetic acid with heat in a solvent, which compound of Formula (III) can optionally be further reacted to cyclize to a compound of Formula (II) pseudothiohydantoins, as defined above, which can optionally be hydrolyzed to a compound of Formula (I) by heating in an aqueous acid.

It has also been found that one method for treating infections caused by the herpes simplex virus comprising administering a therapeutically effective amount of a pharmaceutically-acceptable formulation having as the active ingredient any pharmaceutically-acceptable acid addition salts of metformin, such as the hydrochloride, sulfate, acetate, fumarate, maleate, succinate, or ascorbate salt. These metformin salts can be further used in conjunction with formulations of acyclovir or valacyclovir.

When R and $R_1$ are both H in Formula (I) and the metformin salt is formed, the compound of Formula (IV) below results (JIVA-005):

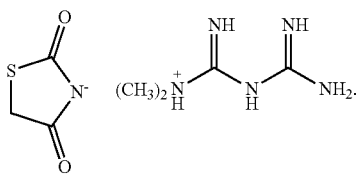

Formula (IV)

When R and $R_1$ in Formula (II) are both H and the metformin salt is formed, the Formula (V) compound below results (JIVA-0049):

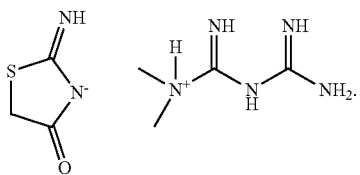

Formula (V)

In a similar manner, metformin salts are made of Formula (I) and Formula (II) compounds above.

In the above Formula (I) or (II) when R is H, and $R_1$ is an omega-3 polyunsaturated fatty acid (PUFA) derivative, which is joined from the methylene moiety formed by reduction of the carboxylic acid of one of the following representative omega-3 polyunsaturated fatty acids, (described in U.S. Pat. No. 9,364,465):

cis,cis,cis-9,12,15-octadecatrienoic acid (ALA), providing RS-5-((9Z,12Z,15Z)-octadeca-6,9,12-trien-1-yl) thiazolidine-2,4-dione, (JIVA-0013);

cis,cis,cis,cis,cis-5,8,11,14,17-eicosapentanenoic acid (EPA), providing RS-5-((5Z,8Z,11Z,14Z,17Z)-eicosa-5,8,11,14,17-pentaen-1-yl)thiazolidine-2,4-dione, (JIVA-002); or cis,cis,cis,cis,cis,cis-4,7,10,13,16,19-docosahexaenoic acid (DHA), providing RS-5-((4Z,7Z,10Z,13Z,16Z,19Z)docosa-4,7,10,13,16,19-hexaen-1-yl)thiazolidine-2,4-dione, (JIVA-004).

The compounds of Formula (I), Formula (II), and Formula (III) may be formulated as such, or as their water soluble salts, such as sodium, potassium, or calcium, or as metforminates.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 represent: Percent reduction of HSV-1 replication following treatment with JIVA compounds 0042 and 005, relative to mock treated control.

DETAILED DESCRIPTION OF THE INVENTION

Figure 1:
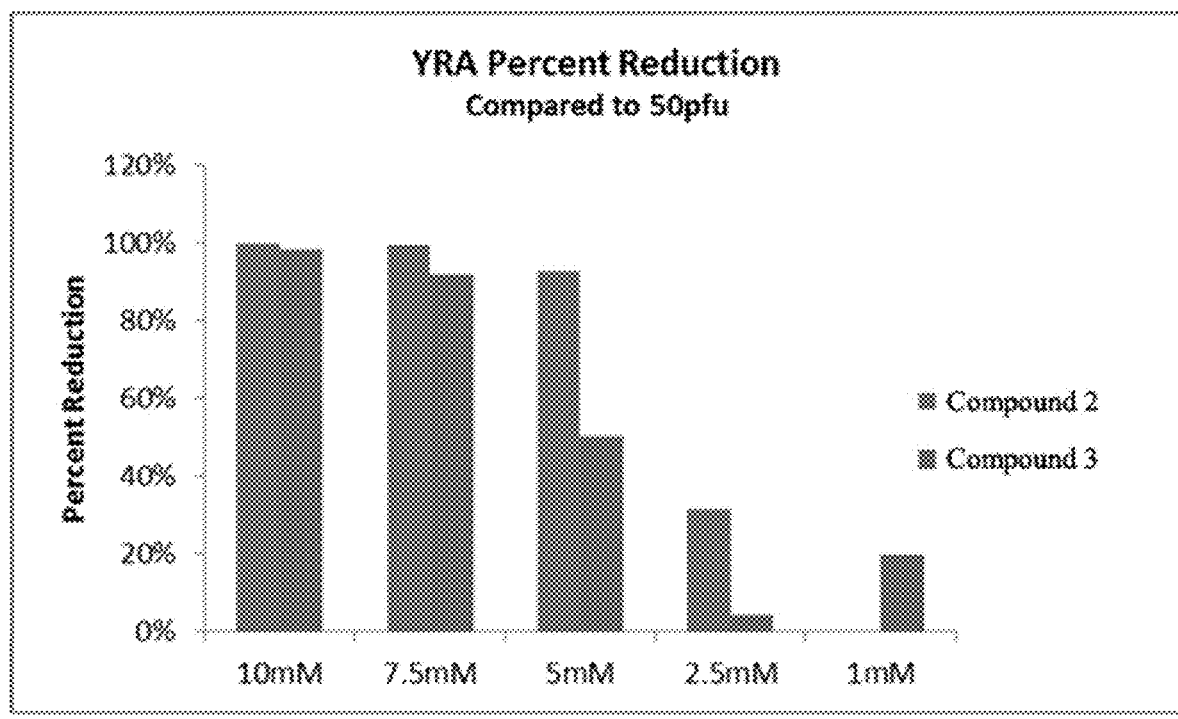
FIG. 1 graphically represents various concentrations (10 mM, 7.5 mM, 5 mM, 2.5 mM, 1 mM) of Compounds 2 and 3 which are JIVA-0042 and JIVA-005, respectively, and their ability to inhibit virus, HSV-2, replication and plaque reduction.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary $CC_{50}$ or CC50 means cytotoxicity concentration of a compound that is often measured by dose response curves assuming the administered doses and intracellular exposures are equal at the time of measurement $EC_{50}$ or EC50 means half maximal effective concentration refers to the concentration of a drug which induces a response halfway between the baseline and maximum after a specified exposure time hsv or HSV means herpes simplex virus(s) and includes HSV-1, 2, 3, HCMV, MCMV, VZV, EBV, and KSHV and others Met.HCL is metformin hydrochloride PFU means a plaque-forming unit YRA means yield reduction assay h means hour(s)

RT means room temperature or ambient temperature mp means melting point

ALA means α-linolenic acid or cis,cis,cis-9,12,15-octadecatrienoic acid

EPA means cis,cis,cis,cis-5,8,11,14,17-eicosapentanenoic acid (EPA)

DHA means cis,cis,cis,cis,cis-4,7,10,13,16,19-docosahexaenoic acid

Omega-3 fatty acids means naturally occurring, straight-chain $C_{16}$-$C_{24}$, all cis; conjugated, polyunsaturated fatty carboxylic acids PUFAs means polyunsaturated fatty acids that are either naturally occurring omega-3 fatty acids or derivatives thereof SI$_{50}$ means selective index JIVA Compounds means various samples of compounds as made and tested in the examples and figures; as described in the examples, JIVA-0042 is a compound of Formula (I) when R and R$_1$ are both H; JIVA-005 is a compound of Formula (IV) when R and R$_1$ are both H and the metformin salt is formed; JIVA-0043 is a compound of Formula (III) when R is H and R$_1$ is F; JIVA-0049 is a compound of Formula (V) when R and R$_1$ are both H and the metformin salt is formed; JIVA-0048 is a compound of Formula (II) where both R and R$_1$ are H The present discovery of small molecules as discussed in the present invention give hope that an early retreat and relief from an incipient shingles infection and HSV-1 and HSV-2 may be possible using oral and/or parenteral therapies.

Published international patent application WO2014/160936, issued as U.S. Pat. No. 9,364,465, Jun. 14, 2016 describes "Thiazolidinediones of Omega-3 Polyunsaturated Acids as New Insulin Sensitizers for Treating Type 2 Diabetes"; and metformin salts and prodrugs of 2,4-thiazolidinedione are the subject of published international patent application WO2015/042495. These are incorporated herein by reference.

Chemical Examples for Compounds of Formula (I), (II) and (III)

This invention will be further clarified by a consideration of the following examples which provides the preparation of or source for obtaining compounds of Formula (I), Formula (II) and Formula (III) which are intended to be purely exemplary of the present invention.

Example 1

2,4-Thiazolidinedione, MW: 117.13, JIVA-0042, may be purchased from Alfa Aesar Chemicals, 99% pure, as a white powder, mp. 121-124° C. Alternatively, it may be synthesized by the procedure of, Ge No Meng et al., *Organic Preparations and Procedures International* 43(3):312-313 January 2011.

Example 2

Metformin hydrochloride, (1,1-dimethylbiguanide hydrochloride), MW: 165.62 may be purchased from Sigma-Aldrich Co. or is prepared by the method in Procèdde preparation de chlorhydrate de dimethylbiguanide. Patent FR 2322860, 1975.

Example 3

Pseudothiohydantoin, MW: 116.14, JIVA-0048, Formula (II) where both R and R$_1$ are H, may be purchased from Sigma-Aldrich Co. 97%; mp 249° C. (decomposition). This compound may also be isolated as an intermediate in Example 1.

Example 4

RS-(Carbamimidoylsulfanyl)(fluoro)acetic acid, or 2-[Amino(imino)methylsulfenyl]-2-fluoroacetic acid: JIVA-0043, an example of a propseudothiohydantoin, Formula (III) where R is H and R$_1$ is F shown by the following structure.

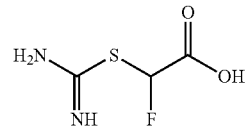

A one-neck round-bottomed flask (25 mL) was charged with ethyl bromofluoroacetate (2.4 mL, 20 mmol), thiourea (1.52 g, 10.0 mmol), and aqueous HBr (4.4 mL, 0.87 M, 1.9 mmol). The reaction mixture was stirred at RT for 24 h. The white precipitate was filtered off, washed with cold acetone (ca. 10 mL), and dried under vacuum to give product as a white solid (1.53 g, 57%). The product was dissolved in hot water (ca. 60-70° C.) and recrystallized at 4° C. to give colorless crystals, which has the following characteristics:

mp 178° C.

MS (ESI, m/z): 153 ([M+H]$^+$, 100%).

HRMS (ESI-TOF) [M+H]$^+$ calcd. for C$_3$H$_6$FN$_2$O$_2$S 153.0134, found 153.0130.

IR (cm$^{-1}$, ATR): 3393 w, 3264 w, 2939 m, 2775 m, 1679 m, 1614 s, 1444 m, 1378 s, 1298 m, 1201 m, 1108 w, 1021 s, 932 w, 760 s, 683 s, 612 s, 498 s, 439 m.

NMR $^1$H (400 MHz, D$_2$O) δ: 6.47 (d, 1H, $^2J_{H\text{-}F}$=52.8 Hz). $^{13}$C (100 MHz, DMSO-d$_6$) δ: 183.1 (d, $^2J_{C\text{-}F}$=14.7 Hz, C=O), 178.7 (C=NH), 98.3 (d, $^1J_{C\text{-}F}$=221.4 Hz, CHF). $^{19}$F (376 MHz, D$_2$O) δ: −153.3 (d, $^2J_{F\text{-}H}$=53.1 Hz).

Elemental analysis: calcd. for C$_3$H$_5$FN$_2$O$_2$S: C, 23.68, H, 3.31, N, 18.41, S, 21.07, F, 12.49.

Found: C, 23.79, H, 3.05, N, 18.30, S, 20.97, F, 11.54.

Example 5

Preparation of Sodium Salt of JIVA-0043

To a 100 mL round-bottomed flask was added 12 mL of methanol, and 1.52 g (0.01 mole) of JIVA-0043 (prepared by the process in Example 3). The mixture was stirred by hand and to the mixture was added 8 mL of 5% w/v solution of aqueous NaOH obtained from Alfa-Aesar. Instantly a deep yellow color appeared. The mixture was evaporated to dryness on a rotary evaporator. The residue was triturated with acetone which was decanted off. The resulting sticky residue was worked up 4× with absolute ethanol, decanting the supernate each time. The bright yellow solid was collected on a funnel and washed with acetone and dried under vacuum at RT to yield 1.37 g.

Elemental analysis: calcd. for C$_3$H$_4$FN$_2$O$_2$S Na: C, 20.69, H, 2.32, N, 16.09, S, 18.41.

Found: C, 19.74, H, 2.84, N, 10.91, S, 17.61.

The compound decomposed on further drying under high vacuum over P$_2$O$_5$.

Single crystal x-ray structure of JIVA-0043

A clear colorless block-like specimen of C$_{12}$H$_{20}$F$_4$N$_8$O$_8$S$_4$, as made above for JIVA-0043, approximate dimensions 0.098 mm×0.251 mm×0.360 mm, was used for the X-ray crystallographic analysis. The X-ray intensity data were measured on a Bruker APEX-II CCD system.

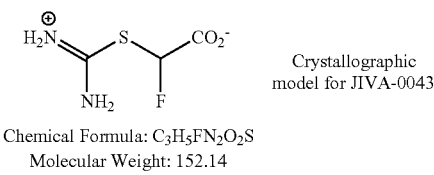

Crystallographic model for JIVA-0043

Chemical Formula: C₃H₅FN₂O₂S
Molecular Weight: 152.14

A total of 3680 frames were collected. The total exposure time was 10.22 h. The frames were integrated with the Bruker SAINT Software package using a narrow-frame algorithm. The integration of the data using a monoclinic unit cell yielded a total of 34883 reflections to a maximum θ angle of 68.68° (0.83 Å resolution), of which 4412 were independent (average redundancy 7.906, completeness=99.0%, $R_{int}$=6.11%, $R_{sig}$=4.14%) and 4183 (94.81%) were greater than 2σ(F²). The final cell constants of a=20.7047(5) Å, b=7.9881(2) Å, c=15.7393(4) Å, β=112.290(1°), volume=2408.62(10) ų, are based upon the refinement of the XYZ-centroids of 9521 reflections above 20 σ(I) with 9.232°<2θ<136.4°. Data were corrected for absorption effects using the multi-scan method (SADABS). The ratio of minimum to maximum apparent transmission was 0.651. The calculated minimum and maximum transmission coefficients (based on crystal size) are 0.4930 and 0.7530.

Figure 8A:
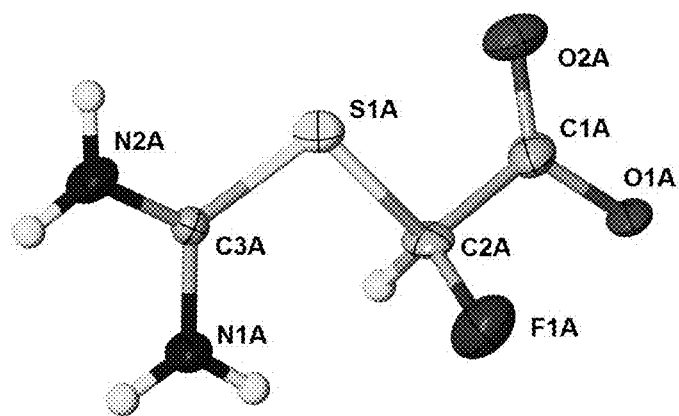
FIG. 8A shows the single crystal x-ray structure of JIVA-0043.

The structure was solved and refined using the Bruker SHELXTL Software Package, using the space group P 1 21/c 1, with Z=4 for the formula unit, $C_{12}H_{20}F_4N_8O_8S_4$. The final anisotropic full-matrix least-squares refinement on F² with 207 variables converged at R1=31.91%, for the observed data and wR2=71.61% for all data. The goodness-of-fit was 4.103. The largest peak in the final difference electron density synthesis was 7.367 e⁻/ų and the largest hole was -2.504 e⁻/ų with an RMS deviation of 0.513 e⁻/ų. On the basis of the final model, the calculated density was 1.678 g/cm³ and F(000), 1248 e⁻. FIG. 8A depicts this single crystal measurement.

| Sample and crystal data for JIVA-0043 | |
|---|---|
| Chemical formula | $C_{12}H_{20}F_4N_8O_8S_4$ |
| Formula weight | 608.60 g/mol |
| Temperature | 100(2) K |
| Wavelength | 1.54178 Å |
| Crystal size | 0.098 × 0.251 × 0.360 mm |
| Crystal habit | clear colorless block |
| Crystal system | monoclinic |
| Space group | P 1 21/c 1 |
| Unit cell dimensions | a = 20.7047(5) Å   α = 900 |
|  | b = 7.9881(2) Å    β = 112.290(1)° |
|  | c = 15.7393(4) Å   γ = 90° |
| Volume | 2408.62(10) ų |
| Z | 4 |
| Density (calculated) | 1.678 g/cm³ |
| Absorption coefficient | 4.447 mm⁻¹ |
| F(000) | 1248 |

Figure 8B:
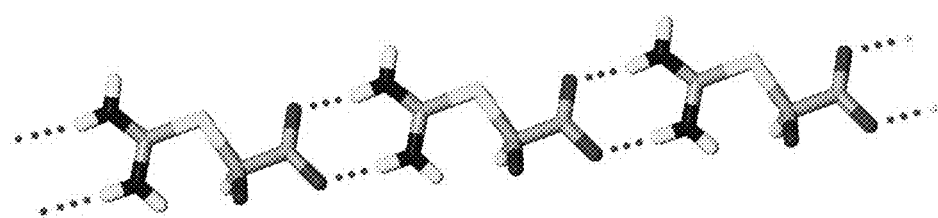
FIG. 8B shows the crystal structure of JIVA-0043 showing the N—H . . . O hydrogen bond network.

FIG. 8B depicts the crystal structure of JIVA-0043 showing the N—H . . . O hydrogen bond network.

Example 6

RS-2-Imino-5-methylthiazolidine-4-one; JIVA-0044, an example of pseudothiohydantoin, Formula (II) where R is H and $R_1$ is methyl

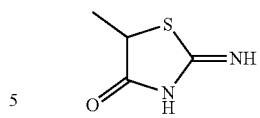

A one-neck round-bottomed flask (25 mL) was charged with 2-chloropropionic acid (1.08 g, 10.0 mmol), thiourea (0.76 g, 10 mmol), and aqueous HBr (4.4 mL, 3.8 mmol). The reaction mixture was stirred at RT for 24 h. The solvent was evaporated, and white precipitate was washed with cold acetone (6 mL), and dried under vacuum to give pure product as a white solid (984 mg, 76%), then recrystallized from hot EtOH-MeOH mixture to give 415 mg. as white needles, which has the following characteristics:

mp: 224-228° C. (d)
MS (ESI, m/z): 131 ([M+H]⁺, 100%)
HRMS (ESI-TOF) [M+H]⁺ calcd. for $C_4H_7N_2OS$ 131.0279, found 131.0284.
NMR ¹H (400 MHz, DMSO-d₆) δ: 10.50 (bs, 1H), 4.38 (q, 1H, ³$J_{HH}$=7.3 Hz), 1.53 (d, 3H, ³$J_{HH}$=7.3 Hz)
¹³C (100 MHz, DMSO-d₆) δ: 180.4, 176.9, 46.8, 177

A single crystal X-ray spectrum of JIVA-0044 was obtained as its HBr salt.

Example 7

RS-2-[Amino(imino)methylsulfenyl]-2-phenylacetic acid; JIVA-0045, an example of a propseudothiohydantoin, Formula (III) where R is —$CO_2H$ and $R_1$ is phenyl:

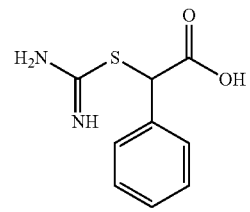 [SMILES: N=C(N)SC(C(=O)O)c1ccccc1]

A one-neck round-bottomed flask (25 mL) was charged with 2-bromo-2-phenylacetic acid (2.15 g, 10.0 mmol), thiourea (0.76 g, 10 mmol), and aqueous HBr (4.4 mL, 3.8 mmol). The reaction mixture was stirred at RT for 17 h. The white precipitate was filtered off and washed with cold EtOH (40 mL) and Et₂O (10 mL), and dried under vacuum to give product as a white solid (1.54 g, 73%) which has the following characteristics:

mp 230° C. (d)
MS (ESI, m/z): 211 ([M+H]⁺, 100%).
HRMS (ESI-TOF) [M+H]⁺ calcd. for $C_9H_{11}N_2O_2S$, 211.0541, found 211.0532.
NMR ¹H (400 MHz, DMSO-d₆) δ: 8.17 (bs, 2H), 7.41-7.23 (m, 5H), 4.26 (s, 1H).
Elemental analysis: calcd. for $C_9H_{10}N_2O_2S$: C, 51.41, H, 4.79, N, 13.32, S, 15.25.
Found C, 51.11, H, 4.75, N, 13.12, S, 15.19.

Example 8

RS-2-Imino-5-phenylthiazolidine-4-one; JIVA-0045A; Example of pseudothiohydantoin, Formula (II) where R is H and $R_1$ is phenyl:

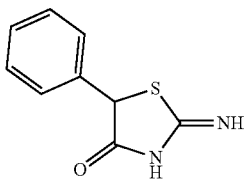 [SMILES: N=C1NC(=O)C(c2ccccc2)S1]

A one-neck round-bottomed flask (25 mL) was charged with 2-bromo-2-phenylacetic acid (2.15 g, 10.0 mmol), thiourea (0.76 g, 10 mmol), and aqueous HBr (4.4 mL, 3.8 mmol). The reaction mixture was stirred at RT for 24 h. The white precipitate was filtered off and washed with cold acetone (6 mL), and dried under vacuum to give pure product as a white solid (1.0 g, 52%), which has the following characteristics:

mp 224-226° C.

MS (ESI, m/z): 193 ([M+H]$^+$, 100%).

HRMS (ESI-TOF) [M+H]$^+$ calcd. for $C_9H_9N_2OS$ 193.0436, found 193.0434.

IR (cm$^{-1}$, ATR): 3191 bw, 2923 bm, 1763 w, 1747 w, 1644 s, 1563 w, 1492 m, 1451 m, 1417 bs, 1275 w, 1193 s, 1175 s, 891 m, 778 m, 757 m, 716 vs, 691 vs, 599 m, 554 s, 509 s, 483 s, 457 s.

NMR $^1$H (400 MHz, DMSO-d$_6$) δ: 9.43 (bs, 1H), 8.98 (bs, 1H), 7.41-7.30 (m, 5H), 5.52 (s, 1H).

$^{13}$C (100 MHz, DMSO-d$_6$) δ: 182.1, 174.6, 137.2, 128.8, 128.3, 125.4, 86.6.

Example 9

RS-2-Imino-5-(2'-chlorophenyl) thiazolidine-4-one or 5-(2-chlorophenyl)-2-imino-1, 3-thiazolidin-4-one or 2-amino-5-(2-chlorophenyl)-1, 3-thiazol-4 (5H)-one; JIVA-0046; Formula (II) where R is H and R$_1$ is 2-chlorophenyl:

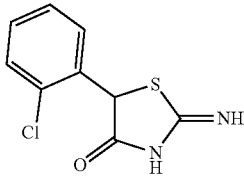 [SMILES: N=C1NC(=O)C(c2ccccc2Cl)S1]

A one-neck round-bottomed flask (25 mL) was charged with 2-bromo-2-(2'-chlorophenyl)acetic acid (2.495 g, 10.00 mmol), thiourea (0.76 g, 10 mmol), and HBr (4.4 mL, 3.8 mmol). The reaction mixture was stirred at RT for 24 h. The white precipitate was filtered off and washed with cold acetone (6 mL), and dried under vacuum to give pure product as a white solid (1.5 g, 66%), which has the following characteristics:

mp 244-246° C.

MS (ESI, m/z): 227 ([M+H]$^+$, 100%).

HRMS (ESI-TOF) [M+H]$^+$ calcd for $C_9H_8ClN_2OS$ 227.0046, found 227.0043.

IR (cm$^{-1}$, ATR): 3263 bm, 2951 bm, 2804 bw, 1688 m, 1656 s, 1505 s, 1474 s, 1442 m, 1373 s, 1264 s, 1249 s, 1174 m, 1127 s, 1038 m, 821 w, 800 m, 764 m, 744 vs, 701 vs, 661 s, 637 s, 626 s, 570 m, 542 w, 511 m, 473 vs, 449 m, 410 m.

NMR $^1$H (400 MHz, DMSO-d$_6$) δ: 9.22 (bs, 1H), 8.97 (bs, 1H), 7.51-7.47 (m, 1H), 7.38-7.31 (m, 3H), 5.70 (s, 1H).

$^{13}$C (100 MHz, DMSO-d$_6$) δ: 186.1, 180.6, 134.7, 133.4, 130.8, 129.8, 129.7, 127.7, 56.5.

Figure 9:
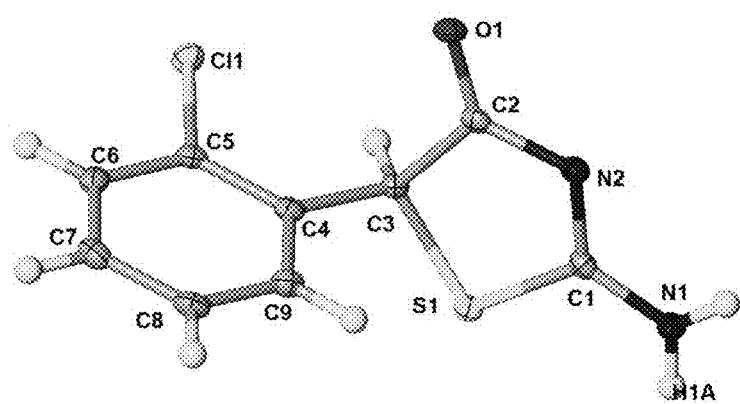
FIG. 9 shows the single crystal X-ray of JIVA-0046.

Single crystal x-ray of JIVA-0046, FIG. 9

A clear colorless prism-like specimen of $C_9H_7ClN_2OS$, approximate dimensions 0.044 mm×0.066 mm×0.112 mm, was used for the X-ray crystallographic analysis. The X-ray intensity data were measured on a Bruker APEX-II CCD system.

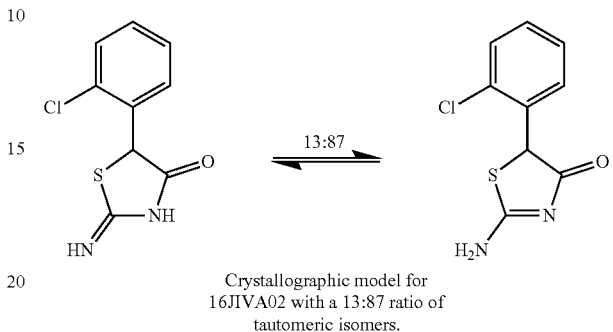

Crystallographic model for 16JIVA02 with a 13:87 ratio of tautomeric isomers.

A total of 5629 frames were collected. The total exposure time was 7.82 h. The frames were integrated with the Bruker SAINT Software package using a narrow-frame algorithm. The integration of the data using a triclinic unit cell yielded a total of 10481 reflections to a maximum θ angle of 68.22 (0.83 Å resolution), of which 1662 were independent (average redundancy 6.306, completeness=97.5%, R$_{int}$=3.90%, R$_{sig}$=2.19%) and 1472 (88.57%) were greater than 2σ(F$^2$). The final cell constants of a=6.9348(3) Å, b=7.3155(2) Å, c=10.8028(3) Å, α=104.284(2)°, β=96.662(2)°, γ=115.460 (2)°, volume=463.82(3) Å$^3$, are based upon the refinement of the XYZ-centroids of 5327 reflections above 20 σ(I) with 8.732°<2θ<136.3°. The ratio of minimum to maximum apparent transmission was 0.828. The calculated minimum and maximum transmission coefficients (based on crystal size) are 0.6240 and 0.7530.

The structure was solved and refined using the Bruker SHELXTL Software Package, using the space group P-1, with Z=2 for the formula unit, $C_9H_7ClN_2OS$. The final anisotropic full-matrix least-squares refinement on F$^2$ with 137 variables converged at R1=2.63%, for the observed data and wR2=6.92% for all data. The goodness-of-fit was 1.053. The largest peak in the final difference electron density synthesis was 0.315 e$^-$/Å$^3$ and the largest hole was −0.216 e$^-$/Å$^3$ with an RMS deviation of 0.054 e$^-$/Å$^3$. On the basis of the final model, the calculated density was 1.623 g/cm$^3$ and F(000), 232 e$^-$.

| Sample and crystal data for JIVA-0046. | | |
|---|---|---|
| Chemical formula | $C_9H_7ClN_2OS$ | |
| Formula weight | 226.68 g/mol | |
| Temperature | 100(2) K | |
| Wavelength | 1.54178 Å | |
| Crystal size | 0.044 × 0.066 × 0.112 mm | |
| Crystal habit | clear colorless prism | |
| Crystal system | triclinic | |
| Space group | P-1 | |
| Unit cell dimensions | a = 6.9348(3) Å | α = 104.284(2)° |
| | b = 7.3155(2) Å | β = 96.662(2)° |
| | c = 10.8028(3) Å | γ = 115.460(2)° |
| Volume | 463.82(3) Å$^3$ | |
| Z | 2 | |
| Density (calculated) | 1.623 g/cm$^3$ | |
| Absorption coefficient | 5.465 mm$^{-1}$ | |
| F(000) | 232 | |

FIG. 9 depicts the molecular structure of JIVA-0046 showing the major tautomeric form and atom-labeling scheme. Displacement ellipsoids are drawn at the 50% probability level.

Example 10

Pseudothiohydantain Metforminate (JIVA-0049), Formula (II) where R and $R_1$ are both H as the metformin salt

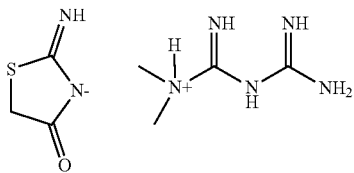

Synthesis of JIVA-0049

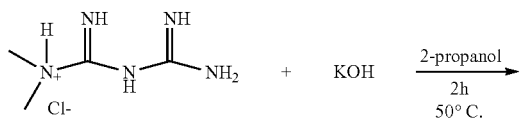

A. Metformin Free Base:

Metformin hydrochloride (AK Scientific, 98% purity, 12.50 g, 75 mmol) was mixed with powdered potassium hydroxide (4.5 g, 80.2 mmol) in 2-propanol at 50-60° C. After 2-3 h, the mixture was cooled to RT and filtered. The solids were washed with 2-propanol (20 mL) and acetone (20 mL). The combined 2-propanol/acetone filtrate was concentrated under reduced pressure on a rotovap. The remaining solid was dissolved in acetone (120 mL), filtered, and concentrated. The experiment produced the free base of metformin (4.8 g, 50% yield) as a white solid, which has the following characteristic:

NMR $^1$H (300 MHz, DMSO-$d_6$) δ 6.4 (br s, 5H), 2.80 (s, 6H).

B. Pseudothiohydantain Salt of Metformin: JIVA0049:

Pseudothiohydantoin (1.0 g, 8.6 mmol) was heated in ethanol (30 mL) to 80° C. under argon. Metformin (1.1 g, 8.6 mmol; prepared above) was added and the solids dissolved. The ethanol solution was cooled to RT and stored overnight at −10° C. After 18 h, no solids had formed. The ethanol was removed under reduced pressure on a rotovap. The remaining solids were mixed with acetone (20 mL) and stirred under argon at RT for 2 h. The solids were filtered, washed with acetone (20 mL), and dried under high vacuum at RT for 24 h. The experiment generated pseudothiohydantain salt of metformin (1.95 g, 92% yield) as a white solid, which has the following characteristics:

| | |
|---|---|
| Analysis: | |
| Appearance: | white solid |
| Chemical Formula: | $C_7H_{15}N_7OS$ |
| Molecular Weight: | 245.31 |
| Chromatographic purity (HPLC): | 99.4% (rt = 3.637 and 4.341 min, 5% MeOH/95% DIUF water to 15% MeOH/85% DIUF water, Luna C18, 5 μ, 4.6 × 150 mm, 1.0 mL/min, 5 μL injection, 40° C., UV detection, 245 nm) |
| NMR $^1$H (300 MHz, DMSO-$d_6$): | δ 7.50-6.50 (br s, 7H), 3.69 (s, 2H), 2.86 (s, 6H). |
| Elemental analysis: | Calculated for $C_7H_{15}N_7OS$: C, 34.27; H, 6.16; N, 39.97; S, 13.07, found: C, 33.68; H, 6.06; N, 38.87; S, 12.49. |

-continued

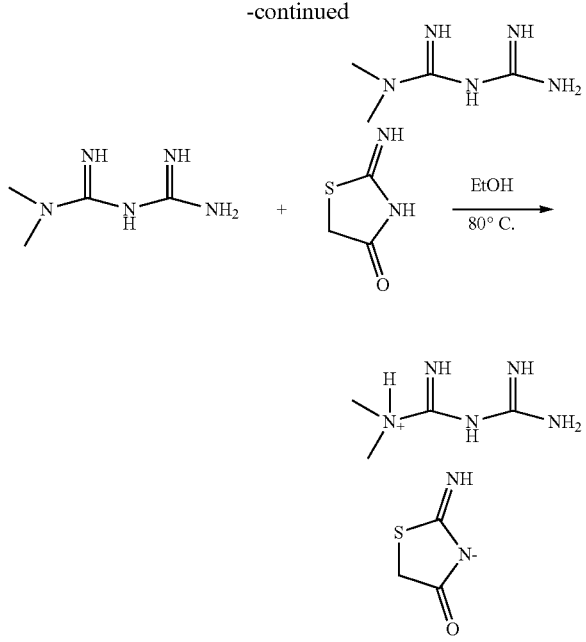

Preparation of PUFA Derivatives

The 2,4-thiazolidinediones (thiohydantoins), in the present invention are depicted in Formula (I), wherein R is H, and $R_1$ is an omega-3 polyunsaturated fatty acid (PUFA) and are the subject matter of the U.S. Pat. No. 9,364,465, incorporated by reference. These are formed by reduction of the carboxylic acid of an omega-3 PUFA to an end primary alcohol (—OH) group, eventually becoming a bridge linked to the 2,4-thiazolidinone ring in the 5-position. Three examples described in U.S. Pat. No. 9,364,465 are: primary alcohols formed by reduction of the carboxylic acid cis,cis,cis-9,12,15-octadecatrienoic acid (ALA); cis,cis,cis,cis,cis-5,8,11,14,17-eicosapentanenoic acid (EPA), and cis,cis,cis,cis,cis,cis-4,7,10,13,16,19-docosahexaenoic acid (DHA).

The alcohol intermediate, cis,cis,cis,cis,cis,cis-4,7,10,13,16,19-docosahexaenoic-1-ol obtained by reduction of DHA in the above series has the same chain-length as 1-docasonol, but has six conjugated-cis-double bonds for a stiff, elongated backbone, in contrast to a floppy backbone in saturated 1-docasanol. Notably, in vitro HSV-2 tests for antiviral activity of DHA derived primary alcohol, using published formulations of 1-docasanol with various surfactants, showed both compounds to be ineffective.

The compounds of Formula (I) where R is H, and $R_1$ is an omega-3 PUFA derivative have a unique 2,4-thiazolidinone pharmacophore, essential for the antidiabetic activity in some popular agents to treat diabetes, and are much more functionalized than a simple long-chain saturated aliphatic alcohol as in 1-docosanol, and the possibility of making water soluble salts such as a sodium salt.

Formulations of the Compounds of Formula (I), (II) and (III):

The present invention uses the compounds of Formula (I), (II) and (III), and their metforminate salts as formulations for the treatment of HSV and VZV caused viral infections. Any suitable pharmaceutically-acceptable formulation designed for the application of the infection can be used for up to a week and have a wide dose range depending on the site of infection, the formulation used and if it is combined with other known drugs, such that does from about 800 mg to about 4 g/day is possible. Examples of such formulations are as follows:

2,4-Thiazolidinedione (Formula I), R and $R_1$ are H, is an off-white solid, mp. 121-124° C., and has an aqueous solubility of 30 mg/mL at 3° C. As an ophthalmic solution, 0.005%, may be prepared as a sterile, isotonic solution with a pH of approximately 6.7. Each mL of the ophthalmic solution, 0.005% contains 13.5 micrograms of 2, 4-thiazolidinedione. Benzyl alkonium chloride, 0.02% is added as a preservative. The inactive ingredients are sodium chloride, sodium dihydrogen phosphate monohydrate, disodium hydrogen phosphate, anhydrous, and water suitable for injection.

Topical, clear gel formulations of pseudothiohydantoin of Formula (II), R and $R_1$ are H, containing 0.25% 0.5% of the active ingredient were prepared as described. The vehicle contains water, propylene glycol, citric acid, sodium dihydrogen phosphate monohydrate, disodium hydrogen phosphate, and hydroxypropylcellulose to achieve a final pH of 4.7-5.1 and viscosity of: 35,000-39,000 cP for good adherence to the site of the lesion.

For topical applications, the formulations of Formula (I), (II) or (III) have one or more pharmaceutically-acceptable adjuvants, binders, gel making or cream making diluents and excipients, e.g., hydroxypropylcellulose, Klucel™ (trademark of HERCULES LLC). For ocular applications, injection water solutions in about 0.005% by wt. concentration may be preserved with benzalkonium chloride (alkyldimethylbenzylammonium chloride), and pH adjusted with sodium dihydrogen phosphate and sodium monohydrogenphosphate.

An Example of a Gel Formulation

A gel formulation of pseudothiohydantoin, JIVA-0048 (Formula (II), R and $R_1$ are H is prepared as follows:

A stock vehicle of 500 g is made using the ingredients in the Table below.

| Ingredient | Weight (g) |
| --- | --- |
| Citric acid monohydrate | 0.650 |
| Dibasic sodium phosphate | 0.763 |
| Monobasic sodium phosphate | 0.431 |
| Mannitol | 6.000 |
| Tween 80 | 0.500 |
| WFI (water) | 300.0 |
| Propylene glycol | 100.0 |
| WFI | QS to 500 |

QS means: as needed
WFI means water for injection or water that is used to dissolve or dilute substances or preparations for parenteral. administration (heat- sterilized WFI)

Figure 10:
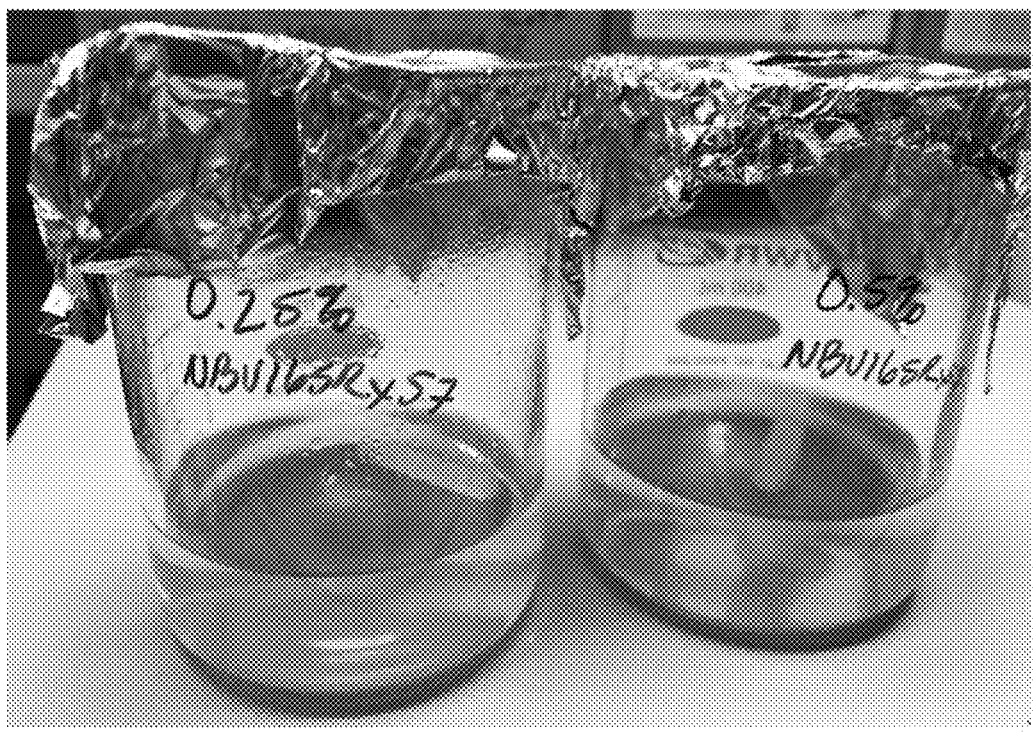
FIG. 10 shows a photograph of a gel formulation of pseudothiohydantoin, JIVA-0048 (Formula (II), R and $R_1$ are H.

To this stock is added pseudothiohydantoin with slow stirring to yield a final concentration of 0.5% or 0.25%. A pale yellow gel results when hydroxyprpoylcellulose (Klucel™) is slowly stirred in. The final pH is 4.7-5.1; viscosity: 35,000-39,000 cP (see FIG. 10).

Two other gels, which contain 2% concn. of JIVA-0048, were prepared. The first gel was made in 50% DMSO with 21% each of propylene glycol and PEG-400. The second gel is made in 25% 1 N NaOH and 20% propylene glycol in water, and PEG-400.

An Example of a Cream Formulation

Creams of 2.5% and 1.25% strength of JIVA-0048 were prepared by dissolving the compound in a hot mixture of water and propylene glycol and then adding with stirring, hydroxypropylcellulose. On cooling to room temperature, a fine cream formed. Microscopic examination of the cream, however, revealed some very fine crystals present in the cream matrix.

The creams or topical application of the present formulations are best used early on the HSV-1 and HSV-2 skin lesions.

An Example of an Ocular Formulation

For ocular applications, 0.005% water solutions may be preserved with benzalkonium chloride, and pH adjusted to 6.7 with sodium dihydrogen phosphate and sodium monohydrogenphosphate.

Injections

For Injections for VZV treatments the injection can be parenterally plus an oral regimen. When the compounds of the present invention have poor aqueous solubility these injections are suspensions.

Formulated Metforminates

The compound of Formula (I), and Formula (II) and Formula (III) may be formulated as metforminates as described in the above examples. A therapeutically effective amount of the solution concentration of active drug is about 10 millimolar (mM) to about 0.01 micromolar (μM).

In Vitro Biology:

General Outline of in vitro biology Study: The overall goal of this study was to perform a preliminary evaluation of gross toxicity as well as antiviral effectiveness against HSV-1 and HSV-2, and VZV virus of several pharmaceutical preparations. The HSV-1 and HSV-2 antiviral activity in an in vitro infection system was studied, at the Louisiana State University, Health Sciences System, in New Orleans, and all three above at the University of Alabama, NIAID sponsored laboratories. These parameters were examined by ascertaining: 1) Determining solubility, and basic chemical parameters required for virological and toxicological assessments; 2) the gross visible toxicity, $CC_{50}$, of JIVA drugs on Vero cell monolayers across a 48 hour continuous treatment window as judged by a relative percentage of cells exhibiting gross signs of toxicity compared to healthy cells; 3) the antiviral activity, $EC_{50}$, of the selected compounds at concentrations that exhibited no visible toxicity across the 48 hour observation window as measured by a viral yield reduction assay.

The yield reduction assay (YRA) was used in determining antiviral activity of test compounds such as JIVA Compounds, controls and standards. The virus yield reduction assay is a powerful technique for evaluating the efficacy of antiviral compounds. Monolayer cultures of mammalian cells were grown in 96-well microliter tissue culture plates and infected with virus. Test compounds were added and serially diluted directly with the plates. Following a cycle of virus replication, culture lysates were made and serially diluted in a separate set of uninfected cultures grown in microliter plates. The cultures were incubated, plaques were enumerated in wells containing 5 to 2.0 plaques, and virus titers were calculated. The known antiviral drug acyclovir was used as reference standard of HSV-2 inhibition.

In virology, PFU means a plaque-forming unit, which is a measure of the number of particles capable of forming plaques per unit volume, such as virus particles. It is a functional measurement rather than a measurement of the absolute quantity of particles: viral particles that are defective or which fail to infect their target cell will not produce a plaque and thus will not be counted.

The concentrations were done in duplicate ranging from 1 mM to 10 mM and the average value is plotted for each concentration. At 2 days post infection the number of plaques were counted. The next day, the wells were collected (media and cells) and titered in a plaque assay.

Results are shown in the graphs (FIGS. 1-6) where: Compound 2 is a compound of Formula (I) when R and $R_1$ are both H, JIVA-0042; Compound 3 is the compound of Formula (I) when R and $R_1$ are both H as a 1:1 metformin salt, JIVA-005; and Met.HCl stands alone (no compound number).

FIG. 1: Both Compound 2 (JIVA-0042) and Compound 3 (JIVA-005) appeared to show toxicity at 10 mM, so even if the graphs show almost 100% reduction at this concentration, it is due to toxicity, perhaps cytostatic inhibition of the cells and thus very few or small plaques were observed. However, by 5 mM of Compound 2 (JIVA-0042), the cells look good (no toxicity) and >95% plaque reduction for Compound 2 and a 50% reduction for Compound 3 (JIVA-005), with the plaques still smaller than the control no drug plaques. This shows that Compound 3 is contributing to the inhibition of virus but that Compound 2 also shows antiviral activity. By 2.5 mM of Compound 2, there is still 30% reduction in virus yield whereas Compound 3 shows very little reduction. By 1 mM no antiviral effect for Compound 2 is detected since plaques are large and similar to the control wells.

Figure 2:
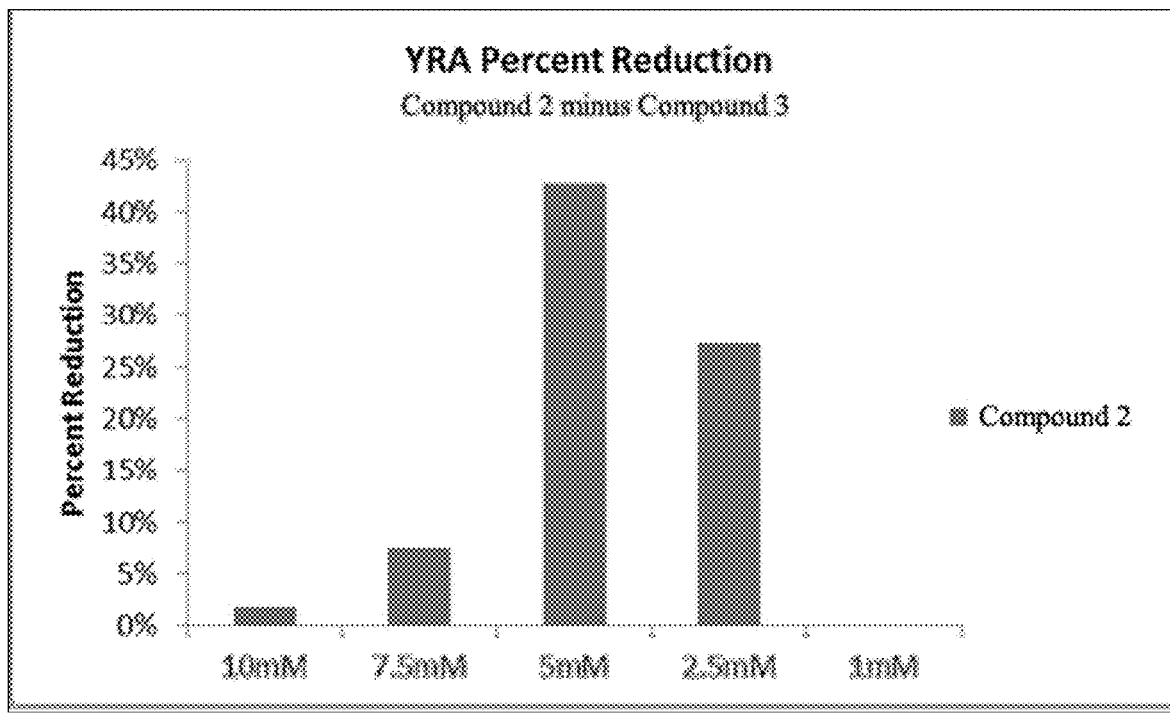
FIG. 2 graphically shows the increased antiviral activity above that detected with JIVA-0042; the amount of inhibition by JIVA-005 alone was subtracted.

FIG. 2: Since Compound 2 (JIVA-0042) shows increased antiviral activity above that detected with alone (Compound 3), the amount of inhibition by Metformin (from it being a component of JIVA-005) was subtracted to show the amount of inhibition due to Compound 2. FIG. 2, at 5 mM of Compound 2, there is approximately 45% inhibition that can be contributed to Compound 2 activity.

Figure 3:
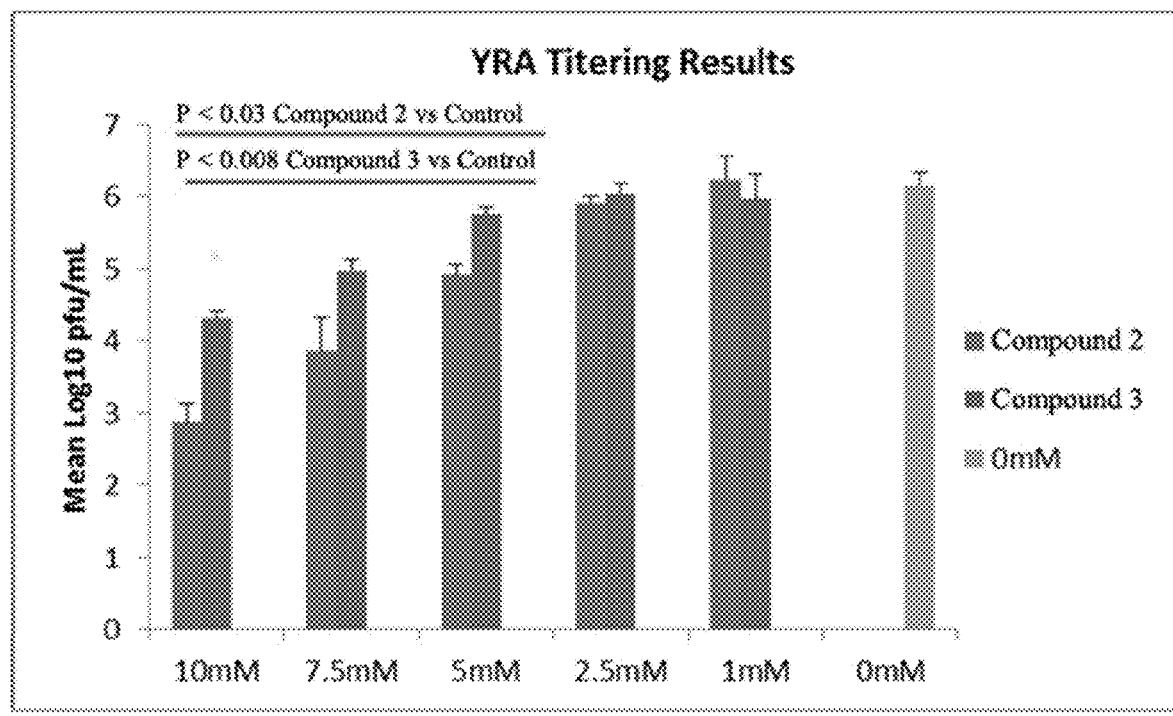
FIG. 3 graphically shows the actual effect of Compound 2, JIVA-0042, or Compound 3, JIVA-005, on virus yield.

FIG. 3: This graph shows the actual effect of Compound 3 (JIVA-005) and Met.HCl on virus yield. After incubation with the drugs, the cells and media were collected and effects of drugs on virus replication were determined. The graphs show the virus titer versus concentration of drugs. At the highest levels of drugs, there are reduced virus titers (but this is mostly due to toxicity). The table below provides the mean titers and p values.

|  | mM | Mean | Stdev | P vs Control |
|---|---|---|---|---|
| Jiva-005 | 10 | 2.87 | 0.04 | 0.00000026 |
|  | 7.5 | 3.86 | 0.12 | 0.0000053 |
|  | 5 | 4.92 | 0.09 | 0.000034 |
|  | 2.5 | 5.90 | 0.08 | 0.025 |
|  | 1 | 6.24 | 0.23 | 0.29 |
| Met. HCl | 10 | 4.32 | 0.06 | 0.0000038 |
|  | 7.5 | 4.97 | 0.10 | 0.000053 |
|  | 5 | 5.76 | 0.10 | 0.0073 |

-continued

|  | mM | Mean | Stdev | P vs Control |
|---|---|---|---|---|
|  | 2.5 | 6.05 | 0.05 | 0.73 |
|  | 1 | 5.98 | 0.01 | 0.10 |
| Control | 0 | 6.07 | 0.06 |  |

Figure 4:
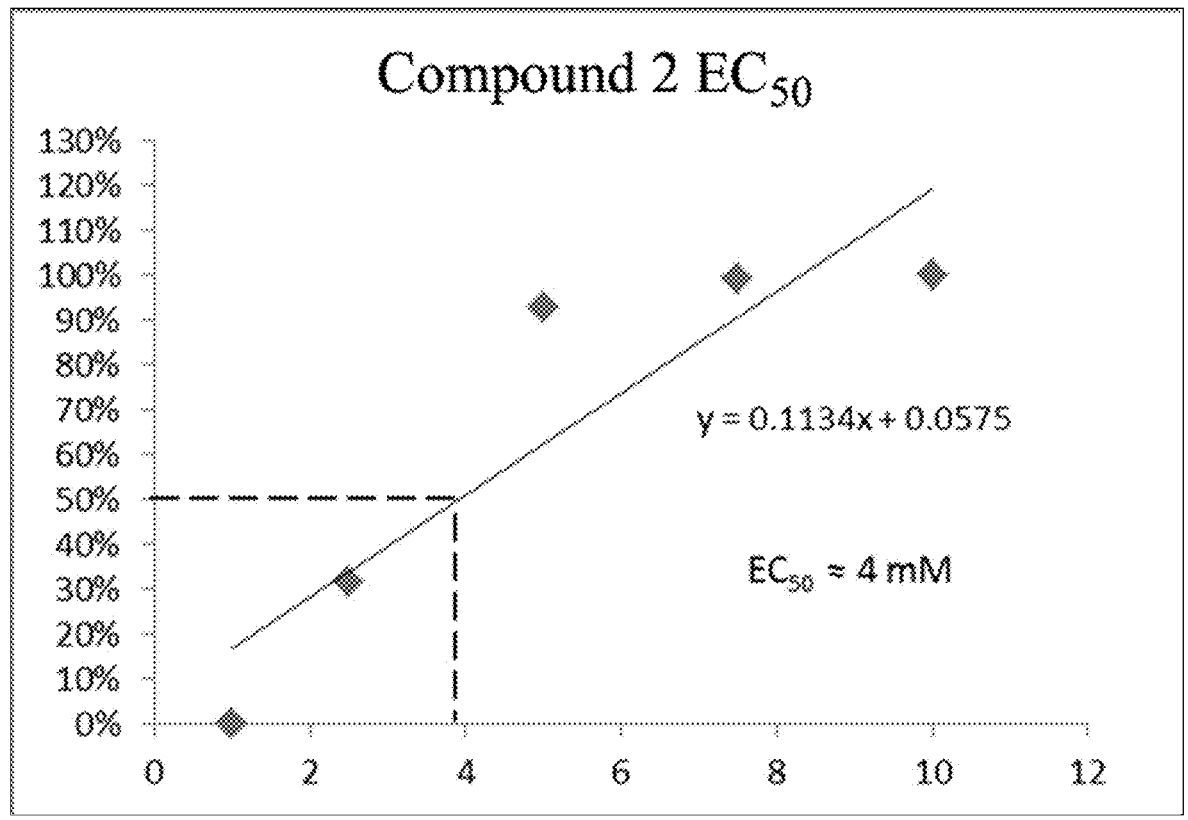
FIGS. 4 and 5 graphically represent estimated EC50s for Compound 2, JIVA-0042, and Compound 3, JIVA-005, using Excel and using a best fit line method.
Figure 5:
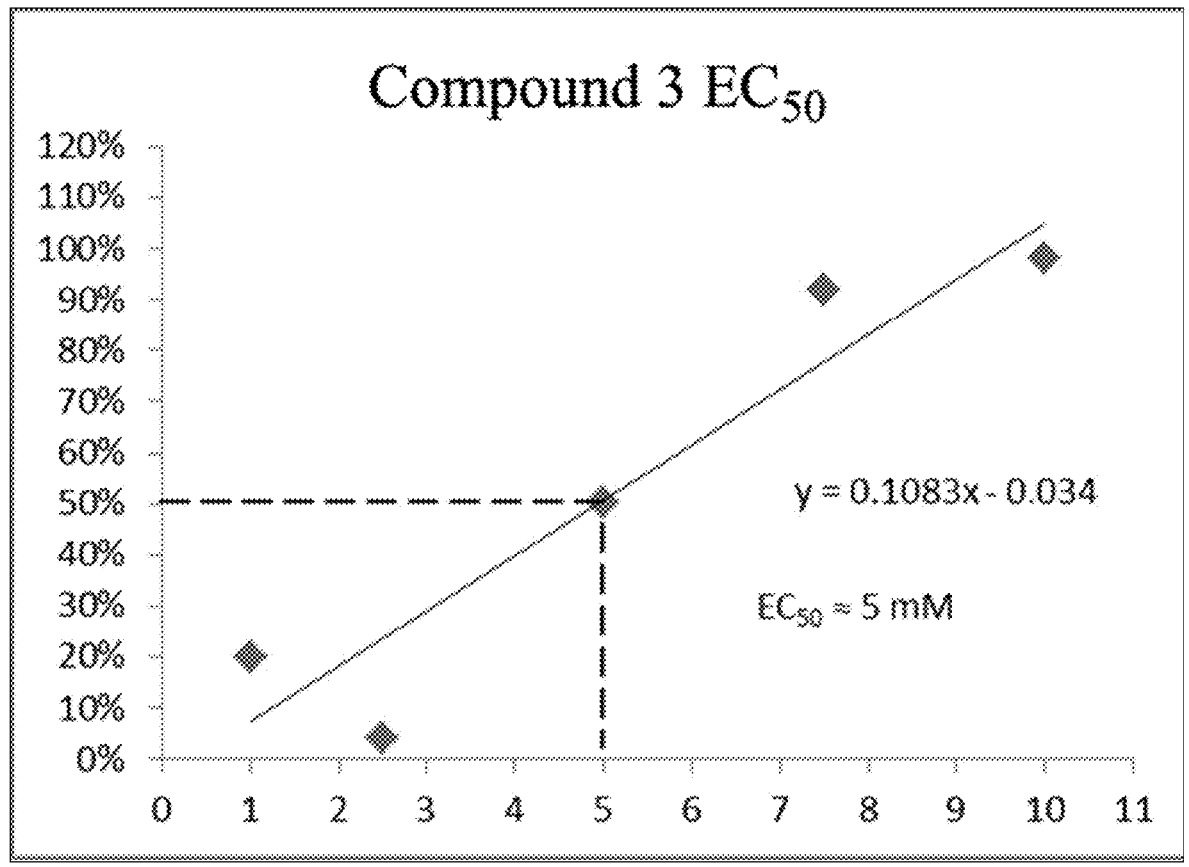

FIGS. 4 and 5: The estimated the $EC_{50}$s for Compound 3 (JIVA-005) and for Met.HCl using Excel and using a best fit line, similar to Compound 2 (JIVA-0042). The estimate the $EC_{50}$ of Compound 3 to be ~4 mM and the $EC_{50}$ for Met.HCl to be ~5 mM.

Figure 6:
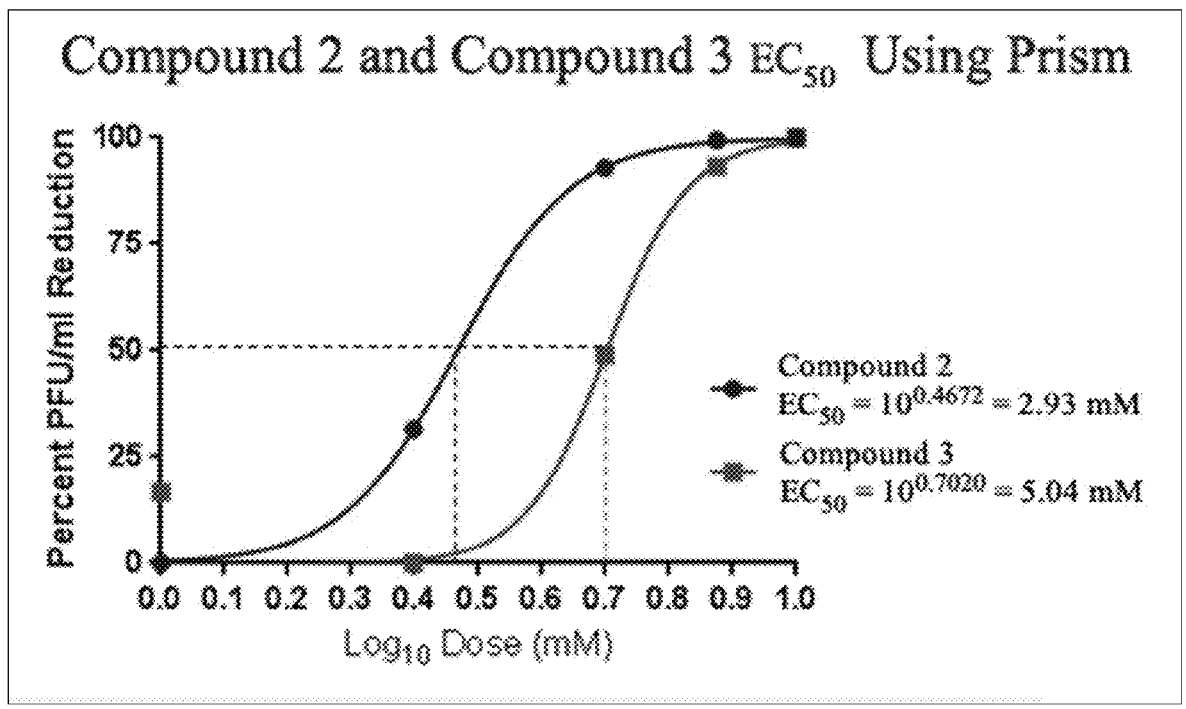
FIG. 6 graphically represents the Prism program determination on EC50 for Compounds 2 (JIVA-0042), 3 (JIVA-005).

FIG. 6: The calculated $EC_{50}$s for Compound 2 and Compound 3 were done using Prism program. Those results showed the $EC_{50}$ for Compound 2 is 2.93 mM, and the $EC_{50}$ for Compound 3 is 5.04 m. This is the better method for determining $EC_{50}$ values. (see FIG. 7) The data for JIVA-0048, the proposed test article for animal efficacy studies, is shown below in a Table form, along with that of other JIVA compounds.

FIG. 7: Shows the results in the percent reduction of HSV-1 replication following treatment with JIVA-0042 and JIVA-005 compounds relative to mock treated control.

Summarizing, JIVA-0042 and JIVA-005 significantly inhibited HSV-1 viral replication when visualized as fold reduction in HSV-1 McKrae viral yield relative to mock treated controls. It is clear that at relatively nontoxic doses of both JIVA-0042 and JIVA-005 compounds, HSV-1 viral yield is reduced by greater than 99.9% (FIG. 7). A 2-fold dilution of each compound from their high concentration showed a greater than 10 fold loss of antiviral activity; however, the reductions were still greater than 1.5 logs. JIVA-0042 showed the greatest efficacy at both concentrations tested with much better activity following a 2 fold dilution than its JIVA-005 counterpart.

Another advantage was noted of thiazolidinedione compounds in Formula (I) where R is H, and $R_1$ is an omega-3 PUFA derivative derived from DHA, EPA or ALA were provided to the Cincinnati Children's Hospital Medical Center, for in vitro HSV-2 antiviral activity by the viral yield reduction assay method, (YRA). These tests showed substantial activity against the HSV-2 virus, but also toxicity to the healthy cells. For the DHA derived (JIVA-004), a ~44% reduction in virus yield was detected at 0.1 mM, and 22% reduction was detected at 0.01 mM. Although virus yield or plaque reduction was detected, a conservative estimated toxicity index CC50 for JIVA-004 of 0.3 mM would result in a selective index $SI_{50}$ of ~3.0, showing a very small window where the drug is active without toxicity. The more water soluble sodium salt of JIVA-004, in the YRA method, was toxic at the highest concentrations tested (10 mM to 7.5 mM).

To explore structure activity relationship, additional novel analogs of Formula (I), Formula (II), and Formula (III), such as JIVA-0043; JIVA-0044; JIVA-0045; JIVA-0046; JIVA-0048 and JIVA-0049 were synthesized. These analogs, along with JIVA-0042 and JIVA-005 were tested at the Louisiana State University (LSU), Health Sciences System, in New Orleans for HSV-1 and HSV-2 antiviral activity using the McKrae viral yield reduction method relative to mock treated controls; and at the NIH for HSV-1 and HSV-2, and VZV antiviral activity by the CellTiter-Glo (Cytopathic effect/Toxicity) assay, using acyclovir as control. The large differences in activity observed in studies at the NIH and LSU may be attributed to prior pH adjustment of solutions of test articles to neutral in the LSU assays.

The antiviral activity test results of the above compounds are summarized in the following Efficacy Table.

In vitro Efficacy Table*

| Tested at | Compound Dose | Virus | $EC_{50}$ (µM) | $CC_{50}$ (µM) | $SI_{50}$ |
|---|---|---|---|---|---|
| A | JIVA-0042 >100 g | VZV | >30 | 80 | <13 |
| A | JIVA-0042 >100 g | HSV-1 | >150 | >150 | 1 |
| A | JIVA-0042 >100 g | HSV-2 | >150 | >150 | 1 |
| L | JIVA-0042 >100 g | HSV-1 | ~625 | >14,000 | ~22 |
| L | JIVA-0042 >100 g | HSV-2 | 1875 | >14,000 | ~7 |
| A | JIVA-005 100 g | VZV | 0.09 | >150 | >1765 |
| A | JIVA-005 100 g | HSV-1 | >150 | >150 | 1 |
| A | JIVA-005 100 g | HSV-2 | >150 | >150 | 1 |
| L | JIVA-005 100 g | HSV-1 | ~625 | >10,000 | ~16 |
| L | JIVA-005 100 g | HSV-2 | ~700 | >10,000 | ~14 |
| A | JIVA-0043 100 g | VZV | <0.05 | >150 | >3125 |
| A | JIVA-0043 100 g | HSV-1 | >150 | >150 | 1 |
| A | JIVA-0043 100 g | HSV-2 | >150 | >150 | 1 |
| L | JIVA-0043 100 g | HSV-1 | >150 | ~1,000 | ~7 |
| L | JIVA-0043 100 g | HSV-2 | >150 | >1,000 | ~7 |
| A | JIVA-0044 1 g | HSV-1 | >150 | >150 | 1 |
| A | JIVA-0044 1 g | HSV-2 | >150 | >150 | 1 |
| L | JIVA-0044 1 g | HSV-1 | 1425 | >39,000 | >28 |
| L | JIVA-0044 1 g | HSV-2 | 1399 | >39,000 | >28 |
| A | JIVA-0045 1 g | HSV-1 | >150 | >150 | 1 |
| A | JIVA-0045 1 g | HSV-2 | >150 | >150 | 1 |
| L | JIVA-0045 1 g | HSV-1 | 238 | 3,600 | 15 |
| L | JIVA-0045 1 g | HSV-2 | ~750 | 3,600 | ~5 |
| A | JIVA-0046 1 g | HSV-1 | >150 | >150 | 1 |
| A | JIVA-0046 1 g | HSV-2 | >150 | >150 | 1 |
| L | JIVA-0046 1 g | HSV-1 | 2,000 | ~1,000 | ~0.5 |
| L | JIVA-0046 1 g | HSV-2 | ~1,000 | ~1,000 | ~1 |
| L | JIVA-0048 >100 g | HSV-1 | 296 | 19,400 | 66 |
| L | JIVA-0048 >100 g | HSV-2 | 76 | 19,400 | 255 |
| A | JIVA-0049 >100 g | VZV | <0.05 | 150 | 3125 |
| N | JIVA-0049 >100 g | HSV-1 | >300 | >300 | 1 |

*means ACV controls were done for all experiments
A is U of Alabama
L is LSU-HSC
N is NIH
~indicates data from a second experiment for that compound and is approximate; solubility issue or DMSO toxicity issue; solubility information is available and pH adjustments are necessary.

Significantly, the test results in the primary assays at the NIH found that the compounds EVA-005 and EVA-0043, and EVA-0049 were highly active against the Varicella-Zoster vines, VZV, which causes chickenpox in children, and shingles in adults, $SI_{50}$ values of >1765 and >3125 for JIVA-005 and JIVA-0043, respectively, vs. >35 for reference acyclovir, were recorded. EVA-0049 showed impressive $EC_{50}$ of <0.05 µM and S150 of 3125.

JIVA-0048 is presently a candidate for in vivo mouse model studies for 1) topical treatment of herpes labialis caused by HSV-1; and 2) HSV-2 caused herpes genitalis in the guinea pig model.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A method of treating persons who have viral infections comprising administering to such persons having infections from herpes simplex viruses (HSV1 or HSV2) or varicella zoster virus (VZV) a therapeutically effective amount of an antiviral agent as a pharmaceutically-acceptable formulation having as an active ingredient a compound of Formula (III), named as propseudothiohydantoins, of the formula:

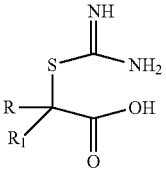

Formula (III)

wherein:

R and $R_1$ are each independently H; F; Cl; $CH_3$; $CF_3$; $C_1$-$C_6$ straight-chain or branched alkyls; $C_6$-$C_{10}$ aryl and when R is H, and $R_1$ is a group as defined above other than H, then both R- and S-stereoisomers are included; and pharmaceutically-acceptable water soluble salts of Formula (III).

2. The method of claim 1, wherein the Formula (III) compound has R is H and $R_1$ is F.

3. The method of claim 1, wherein the Formula (III) compound has R is H and $R_1$ is F as its sodium salt.

4. The method of claim 1, wherein the formulation is suitable for being applied topically as a clear gel or cream ointment, as an ophthalmic solution, or administered systemically.

5. The method of claim 4 wherein the formulation is for ocular administration as an ointment or liquid or for topical administration as an ointment, or injection, having one or more pharmaceutically-acceptable adjuvants, binders, or gel or cream diluents, and excipients.

6. The method of claim 1 wherein the pharmaceutically-acceptable water soluble salts are sodium, potassium or calcium salt.

7. The method of claim 1, wherein ocular herpes infections, herpes genitalis, or shingles infections are treated using the formulation in the form of a solution, gel or cream for topical applications over the site of infected areas.

8. The method of claim 1, wherein the compound is ≥95% chemical purity.

* * * * *